United States Patent [19]

Jeunehomme

[11] 4,381,452
[45] Apr. 26, 1983

[54] SYSTEM FOR MEASURING TRACE MOISTURE IN A GASEOUS STREAM

[75] Inventor: Michel L. Jeunehomme, Darien, Ill.

[73] Assignee: GCA Corporation, Bedford, Mass.

[21] Appl. No.: 231,303

[22] Filed: Feb. 4, 1981

[51] Int. Cl.³ .................. G01T 3/00; G01N 23/09
[52] U.S. Cl. .................................... 250/392; 73/29
[58] Field of Search ............... 73/29; 250/308, 356, 250/390, 392

[56] References Cited

U.S. PATENT DOCUMENTS

| | | | |
|---|---|---|---|
| 2,567,057 | 9/1951 | Crumrine | 250/83.6 |
| 3,122,124 | 2/1964 | Yocum | 116/117 |
| 3,167,947 | 2/1965 | Crawford | 73/23.1 |
| 3,257,842 | 6/1966 | Lerner | 73/53 |
| 3,263,492 | 8/1966 | Lerner | 73/53 |
| 3,315,518 | 4/1967 | Charlson et al. | 73/29 |
| 3,377,294 | 4/1968 | Davis et al. | 252/408 |
| 3,524,062 | 8/1970 | Rocoplan et al. | 250/83.1 |
| 3,532,883 | 10/1970 | Dresia et al. | 250/83.1 |
| 3,577,158 | 5/1971 | Hahn | 250/43.5 |
| 3,600,574 | 8/1971 | Glaza et al. | 250/45 |
| 3,748,473 | 7/1973 | Chen | 250/392 |
| 3,761,712 | 9/1973 | Listerman | 250/388 |
| 3,774,034 | 11/1973 | Martin | 250/388 |
| 3,800,141 | 3/1974 | Beumer et al. | 250/391 |
| 3,955,087 | 5/1976 | Ashe | 250/360 |
| 4,131,011 | 12/1978 | Ling | 73/29 |

OTHER PUBLICATIONS

Product Bulletin 3000-11 (11-76) entitled "Continuous Trace Moisture Analyzer", Totco Division of Baker International Corporation.
Product Bulletin NMG-1 entitled "Ohmart-Nuclear Moisture Gage", The Ohmart Corporation.

Primary Examiner—Howard A. Birmiel
Attorney, Agent, or Firm—Kenway & Jenney

[57] ABSTRACT

A sample fluid stream passes through a molecular sieve in which moisture is adsorbed in direct proportion to the moisture in the fluid stream. Fast neutrons beamed through the sieve interact with the hydrogen nuclei in the accumulated water. The resulting slow neutrons are detected to produce an output indicative of the percentage of moisture in the fluid stream.

10 Claims, 1 Drawing Figure

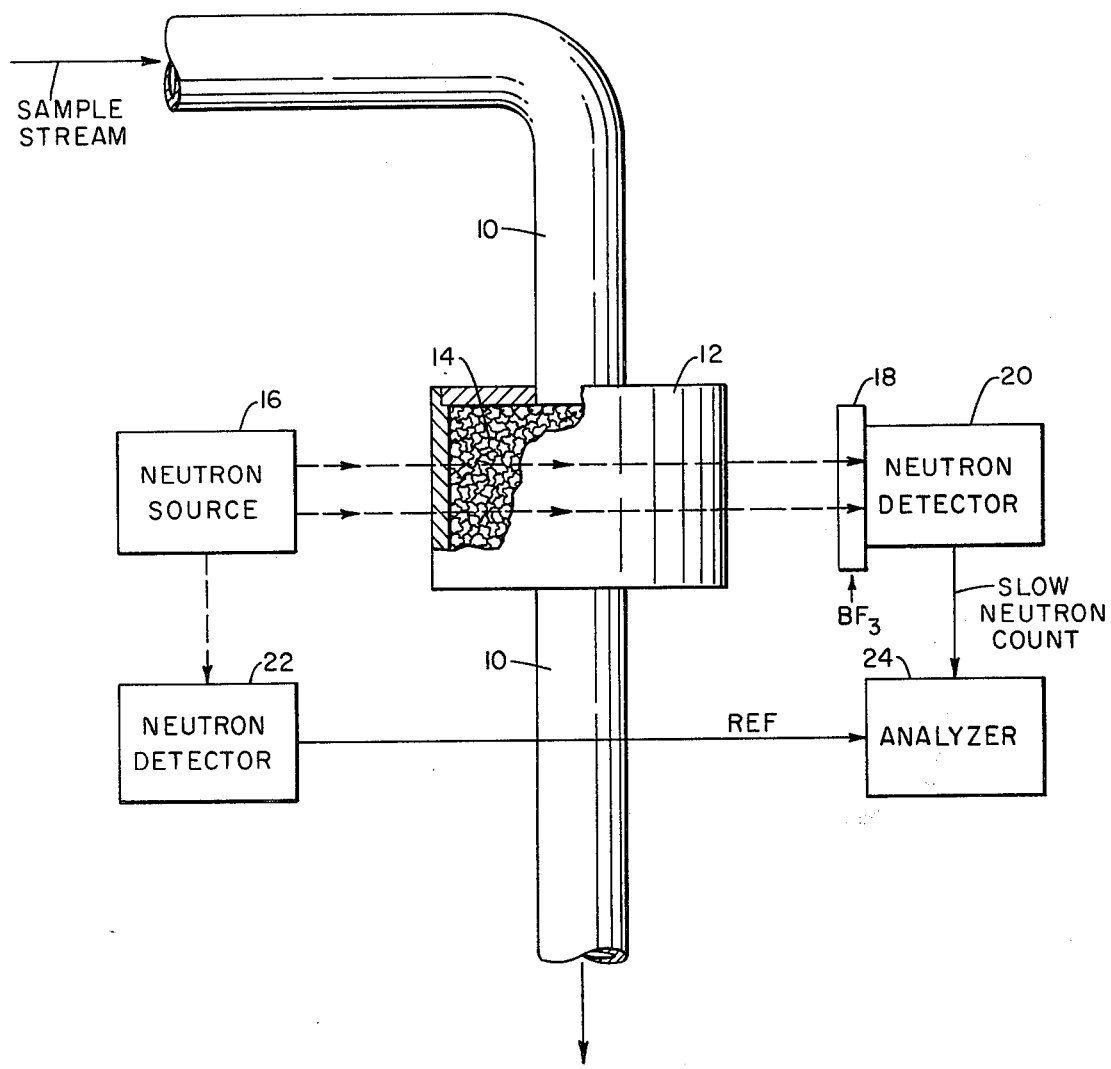

SYSTEM FOR MEASURING TRACE MOISTURE IN A GASEOUS STREAM

BACKGROUND OF THE INVENTION

The invention relates generally to moisture detecting systems and more particularly to instrumentation for measuring trace moisture in a sample fluid stream.

The need arises in connection with chemical processing, for example, at refineries, to keep track of extremely small percentages of water or water vapor present in a fluid stream. In certain applications continuous accurate measurement of trace moisture in fluids is necessary to meet product and corrosion specifications. For example, accurate control of the moisture level in hydrogen recycle gas is necessary to assure optimum catalyst life.

Process moisture analyzers are known in which a sample gaseous stream is placed in contact with a dielectric desiccant in an electrical capacitance cell. The capacitance varies as a function of the amount of water in the desiccant. To measure water in solids, another type of moisture analyzer, based on an entirely different principle, makes use of the ability of hydrogen nuclei, which are abundant in water, to slow down fast neutrons to thermal energies. Wood chips, paper and other bulk material are analyzed by this technique in which a neutron source irradiates material carried on a conveyor belt. A detector located beneath the conveyor senses slow neutrons indicative of water. This type of gauge would not be suitable for trace moisture detection because of the low incidence of water molecules. Nor could it differentiate hydrogen gas, for example, from water vapor.

The prior art capacitance cell technique for trace moisture detection in a sample stream suffers from the disadvantage that the sensitivity of the dielectric constant to the presence of water is easily affected by impurities.

One of the specific applications for trace moisture analysis is gaseous streams of hydrocarbons or hot hydrogen gases containing a trace of water vapor. Because of the critical effect of water vapor in the processes involving gaseous streams of this kind, the unreliability of the capacitance cell instrument is a major drawback.

SUMMARY OF THE INVENTION

Accordingly, the general purpose of the invention is to detect trace quantities of moisture in fluid streams without the shortcomings of prior art instruments. The goal is to provide a process moisture analyzer which is significantly less vunerable to the effects of impurities, and the specific objective of the invention is to measure low moisture levels in a gaseous steam containing atomic or molecular hydrogen more accurately and reliably than in the past.

These and other objects of the invention are achieved by the novel irradiated molecular sieve system according to the invention. A sample fluid stream passes through a molecular sieve in which moisture is adsorbed in direct proportion to the moisture in the fluid stream. Fast neutrons beamed through the sieve interact with the hydrogen nuclei in the accumulated water. The resulting slow neutrons are detected to produce an output indicative of the percentage of moisture in the fluid stream.

BRIEF DESCRIPTION OF THE DRAWING

The single FIGURE is a schematic and block diagram illustrating the process moisture analyzer according to the invention.

DETAILED DESCRIPTION

In the diagram a pipe 10 carries a sample fluid stream, for example, a side stream or slipstream diverted from a main stream, for example, containing heated hydrogen ($H_2$) recycle gas with a trace of moisture. The pipe 10 is coupled in series with a fluid-tight canister 12 containing a suitable moisture adsorbent material 14. This material is preferably in the form of a molecular sieve made of sintered, activated alumina or silicagel or an equivalent passive desiccant material. As the fluid flows through the pipe 10, it must pass through the molecular sieve 14 in the canister 12. Due to the behavior of the molecular sieve in a fluid stream, instead of continuously accumulating water until a saturation point is reached, water accumulates until an equilibrium point is attained in relation to the partial vapor pressure of trace moisture entrained in the fluid stream. Once this point is achieved, equilibrium is maintained by balanced adsorption and evaporation. If the moisture content of the stream increases or decreases, a new higher or lower equilibrium point will be sought and established by the molecular sieve. At these equilibrium points, the relative quantity of water in the sieve is proportional to the current moisture content of the sample stream.

The remaining components in the diagram continuously measure the equilibrium quantity of water in the molecular sieve 14. A neutron source 16, such as plutonium, produces fast (4 to 6 MeV) neutrons which are beamed through the canister 12. The beam is intercepted on the other side of the canister 12 by a boron trifluoride ($BF_3$) shield 18. Fast neutrons are absorbed by the shield. Slow neutrons at thermal energies pass to a neutron detector 20 whose output represents the number of detected neutrons per unit time. The shield 18 and neutron detector 20 are commercially available as a $BF_3$ proportional counter.

The measurement of the equilibrium quantity of water in the molecular sieve 14 exploits the property of hydrogen atoms to slow down fast neutrons. Interacting with the hydrogen nuclei in the accumulated water, the incoming fast neutrons are relieved of most of their energy and sent on as slow neutrons. Fast neutrons which escape collison are quenched by the $BF_3$ shield 18. The more water present in the canister 12, the more collisions take place between fast neutrons and hydrogen nuclei and consequently the more slow neutrons are detected.

In order to normalize the reading with respect to the intensity of the neutron beam incident on the canister 12, another neutron detector 22 receives an unimpeded sample of neutrons from the neutron source 16 proportional in intensity to the neutron beam passing through the canister 12. In an analyzer 24 the slow neutron count from the detector 20 is referenced to the unimpeded fast neutron count from the detector 22. The analyzer 24 may be a conventional digital or an analog computing circuit and display (not shown) to provide a continuous reading proportional to the trace moisture content in the sample stream.

Even where the gaseous sample stream is composed predominantly of hydrocarbons or molecular hydrogen itself, the above-described method is accurate. At any time, the amount of water per irradiated unit volume in the canister 12 is far greater than the amount of hydrogen contained in the gaseous stream flowing through the same volume. Nevertheless, it may be desirable in certain applications to run a parallel sample stream through a drier, to calibrate the measuring system.

The equilibrium quantity of water is temperature but not time-dependent. The temperature is a function of the sample stream temperature, the moisture content and the type of moisture adsorbent material 14. Because equilibrium is temperature-dependent, it may be desirable in certain applications to insert a thermostatically controlled pre-heater upstream of the molecular sieve.

In certain applications the above-described system may be limited by the presence of specific impurities which appear to alter the adsorption characteristics of the molecular sieve. The affinity for water is such that at equilibrium the molecular sieve contains more water than any other material. While this property makes the instrument sensitive to variations of a few parts per million by acting as a moisture concentrator, a change in adsorption characteristics can significantly alter the amount of water retained. If the process stream contains impurities having this effect on the selected desiccant, the impurities should be filtered or scrubbed from the sample stream upstream from the desiccant if the problem cannot be eliminated by choice of a different desiccant material.

In addition to testing hydrocarbon and hydrogen gases, the system of the invention is designed to serve as a trace moisture analyzer in all applications formerly served by capacitance cell instruments, for gases such as chlorine, freon, air and sulphur dioxide and for liquids such as gasoline, butadiene, oil and freon.

The foregoing description is intended to be generally illustrative of the principles of the present invention. Other applications and variations in the preferred components of the system may be made without departing from the scope of the invention as indicated by the appended claims.

What is claimed is:

1. A system for measuring trace moisture in a fluid stream, comprising
    moisture-adsorbent means for accumulating moisture to an equilibrium point proportional to moisture content of said fluid stream,
    means for continuously directing at least a representative portion of said fluid stream through said moisture-adsorbent means,
    means for irradiating said moisture-adsorbent means with fast neutrons, and
    means for detecting slow neutrons coming from said moisture-adsorbent means indicative of interaction with hydrogen nuclei.

2. The system of claim 1, further comprising
    means responsive to said detecting means for indicating the number of detected slow neutrons from said moisture-adsorbent means to produce a reading indicative of the trace moisture level in said fluid stream.

3. The system of claim 2, wherein said irradiating means includes a source of fast neutrons located outside said stream to one side of said moisture-adsorbent means.

4. The system of claim 3, further comprising means for normalizing the output of said indicating means with respect to the activity of said neutron source including
    another neutron-detecting means arranged to receive neutrons from said neutron source prior to striking said moisture-adsorbent means for producing a reference output, and
    analyzer means for providing a reading indicative of trace moisture in said fluid stream as a function of the output of said slow neutron indicating means relative to the reference output of said other neutron-detecting means.

5. The system of claim 1, wherein said moisture-adsorbent means includes a molecular sieve.

6. The system of claim 5, wherein said molecular sieve is made of activated sintered alumina.

7. The system of claim 1, wherein said moisture-adsorbing means is a desiccant.

8. The system of claim 1, wherein said means for directing a portion of the fluid stream includes a pipe and said moisture-adsorbent means includes a fluid-tight container filled with a moisture-adsorbent material connected in line with and in gaseous communication with said pipe.

9. The system of claim 1, wherein said fluid stream comprises heated hydrogen gas with a trace of moisture.

10. The system of claim 1, wherein said fluid stream comprises a hydrocarbonaceous fluid with a trace of moisture.

* * * * *